(12) United States Patent
Gloor et al.

(10) Patent No.: US 7,253,297 B2
(45) Date of Patent: Aug. 7, 2007

(54) ASTAXANTHIN ESTERS

(75) Inventors: Arnold Gloor, Basel (CH); Werner Simon, Riehen (CH)

(73) Assignee: DSM IP Assetts B.V., TE Heerlen (NL)

( * ) Notice: Subject to any disclaimer, the term of this patent is extended or adjusted under 35 U.S.C. 154(b) by 0 days.

(21) Appl. No.: 10/503,696

(22) PCT Filed: Jan. 29, 2003

(86) PCT No.: PCT/EP03/00873

§ 371 (c)(1),
(2), (4) Date: Aug. 5, 2004

(87) PCT Pub. No.: WO03/066583

PCT Pub. Date: Aug. 14, 2003

(65) Prior Publication Data

US 2005/0096477 A1    May 5, 2005

(30) Foreign Application Priority Data

Feb. 6, 2002   (EP) .................................. 02002728

(51) Int. Cl.
  *C07C 69/56*    (2006.01)
  *C07C 229/06*   (2006.01)
  *C07C 69/34*    (2006.01)
  *A23L 1/30*     (2006.01)
(52) U.S. Cl. ..................... 558/260; 560/155; 560/190; 426/72
(58) Field of Classification Search ................. 560/8, 560/9, 19, 115, 129, 157; 564/123, 192
See application file for complete search history.

(56) References Cited

U.S. PATENT DOCUMENTS

| 4,871,551 A |   | 10/1989 | Spencer |         |
|-------------|---|---------|---------|---------|
| 5,863,953 A | * | 1/1999  | Luddecke et al. | 514/691 |

FOREIGN PATENT DOCUMENTS

| DE | 4430289    | * | 3/1995  |
|----|------------|---|---------|
| DE | 199 50 327 |   | 4/2000  |
| DE | 19950327   | * | 4/2000  |
| EP | 0 356 499  |   | 7/1990  |
| EP | 0 845 503  |   | 3/1998  |
| JP | 1-202261   |   | 8/1989  |
| JP | 01202261   | * | 8/1989  |
| WO | WO 00/62625|   | 10/2000 |

OTHER PUBLICATIONS

Andersson, T. et al., "Absolute Configurational Assignment of 3-Hydroxycarotenoids," *J. Chem. Soc., Perkin Trans. 1*, vol. 15, pp. 2409-2414 (2000).

Derwent English language abstract of DE 199 50 327 (document B1 above).

* cited by examiner

*Primary Examiner*—Karl Puttlitz
(74) *Attorney, Agent, or Firm*—Bryan Cave LLP

(57) ABSTRACT

Astaxanthin derivatives of the general formula (I) wherein R is in each case group —NH—CH($R^1$)—COO$R^2$, —O$R^3$ or —(Y)$_n$-Z and $R^1$, $R^2$, $R^3$, Y, Z and n are significances given in detail in the description, are novel compounds with improved stability during extrusion at the elevated temperatures as required in feed manufacture and during the storage of the manufactured feed and which accordingly are useful as pigmenting carotenoids for feed for aquatic animals. The derivatives are produced by reacting astaxanthin with the pertinent acid RCOOH as such or as its acid chloride RCOCl or acid anhydride (RCO)$_2$O, or, in the cases where R signifies a group —NH—CH($R^1$)—COO$R^2$, with the appropriate N-carbonyl-amino acid ester of the formula OCNCH($R^1$)COO$R^2$. The invention also concerns a formulation containing such an astaxanthin derivative as the pigmenting carotenoid for use in a feed for aquatic animals, a process for producing such a formulation by dissolving the astaxanthin derivative in a plant or vegetable oil or fat, or in an organic solvent, or in a mixture of both a plant or vegetable oil or fat and an organic solvent, emulsifying the solution with an aqueous solution of a protective colloid, at least partially removing the solvent and water to afford a concentrated emulsion, and spray-drying the concentrated emulsion to finally produce a formulation suitable for incorporation in a feed for aquatic animals, and a feed for aquatic animals containing such a pigmenting carotenoid.

16 Claims, No Drawings

ASTAXANTHIN ESTERS

This application is the National Stage of International Application No. PCT/EP03/00873, filed Jan. 29, 2003.

Carotenoids are a group of naturally occurring organic pigments that are responsible, e.g., for the red, orange and yellow colours in the skin, flesh, shell and exoskeleton of aquatic animals.

The major carotenoid in the aquatic system is astaxanthin, and the function of astaxanthin in aqua culture (aquatic animals) is twofold. Firstly, it can be mobilized and utilized during maturation and at times of stress by certain fish species, e.g. salmonides (salmon and trout), which have evolved systems of deposition and storage of astaxanthin in their flesh; being a natural biological antioxidant, astaxanthin is more efficient than either vitamin E or beta-carotene in this regard. Secondly, astaxanthin is a natural flesh and skin colorant in aquatic animals. The distinctive pink-red flesh colour of for example salmonides and many crustaceans attributed to astaxanthin plays an important role in the aesthetic attraction of the finished food product: the colour is part of the culinary appeal of for example salmonides, shrimps and also red sea bream. Astaxanthin is responsible for this coloration, and because fish and crustaceans cannot themselves synthesize astaxanthin, they rely on a dietary intake for their coloration. Under intensive culture conditions, astaxanthin is normally included in the complete feed for salmonides in order to intensify the desired flesh colour. This is essential if the farmed fish product is to mimic its wild counterpart and have maximum appeal to consumers, whose buying choice is generally influenced by the visual appearance of such products.

Throughout the growth cycle of aquatic animals the pigmentation of the flesh is influenced by a number of exogenous and endogenous factors. Collectively these factors lead to a high variation of flesh pigmentation in any one population of a fish or crustacean species.

The deposition of astaxanthin in the flesh of salmonides is known to be influenced by several endogenous factors. These include the digestibility of the astaxanthin, its absorption from the intestine, its transport into the blood by lipoprotein, its metabolism and its attachment to the muscle fibre. Each factor can significantly influence the astaxanthin concentration in the flesh and the colour visualisation, and a limitation in any of these processes may result overall in insufficient flesh pigmentation.

The utilized form of astaxanthin, i.e. the compound as such or a derivative thereof as a source of astaxanthin, and the raw material matrix (feed) in which it is present influence the digestibility of the pigment and its subsequent efficacy in flesh pigmentation. The digestibility of astaxanthin or a derivative thereof influences in turn the appropriate dietary inclusion rate and the regime employed for flesh pigmentation. Indeed, the form and the diet composition have been shown to affect the digestibility. It has been established that feeding non-formulated astaxanthin leads to almost no pigmentation effect.

Moreover, the apparent digestibility coefficient of nature-identical astaxanthin, astaxanthin dipalmitate and canthaxanthin fed to rainbow trout, Atlantic salmon and sea trout have been shown to exhibit large variations in digestibility, which have been linked to the degradation of the carotenoid during feed extrusion and/or feed storage, or, after feeding, to the degradation of the carotenoid in the gut or to the incomplete extraction of the carotenoid from the contents of the intestines.

As regards the destruction (degradation) of the astaxanthin during feed extrusion, it has been established that the elevated temperatures at which such processing occurs contribute significantly thereto, whereas the degradation during storage is mainly influenced by the exposure to the oxygen in the air.

In these circumstances there is a need to produce new astaxanthin derivatives with improved stability during the extrusion at the elevated temperatures required in feed manufacture and during the storage of the manufactured feed, thus eliminating excessive loss of the active substance during extrusion and storage. Furthermore, the use of a more stable astaxanthin derivative as a pigment in aquaculture could considerably lessen or even eliminate the varying colour quality resulting from the use of astaxanthin or a derivative thereof of less stable nature, as often observed in the past, for example in the flesh of salmon and trout. Moreover, a more stable pigment would allow the fish or crustacean feed manufacturer a greater scope in varying the processing conditions during the feed manufacture, and also the ambient conditions during the storage of the feed, than was possible previously with astaxanthin itself or previously used derivatives thereof. The above-indicated advantages achievable with new astaxanthin derivatives would be significant based on the previous unsatisfactory experience with astaxanthin. Thus it has been observed in the past that 10 to 20% of the pigment is lost by degradation during extrusion at elevated temperatures, and that during the storage of the manufactured feed about 2% of the contained pigment are lost per week through the degradation under ambient conditions.

Accordingly, the present invention provides new astaxanthin derivatives of the general formula I

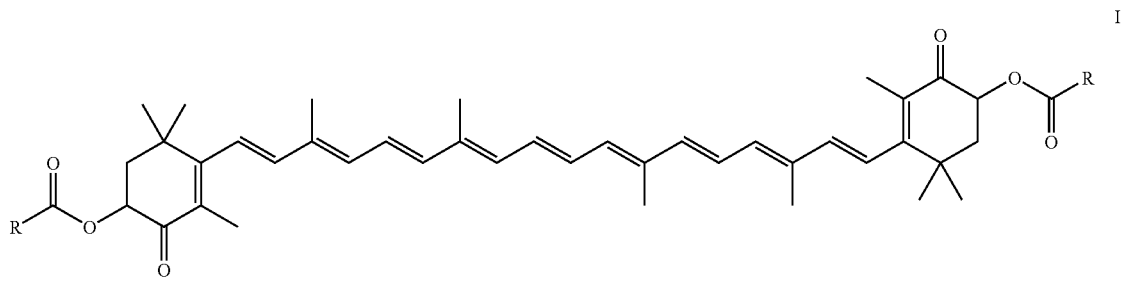

wherein

R is in each case a group (a), (b) or (c)
—NH—CH($R^1$)—COO$R^2$ (a)
—O$R^3$ (b)
—(Y)$_n$—Z (c)

$R^1$ signifies hydrogen or the residue of a protein-forming amino acid, $R^2$ signifies $C_{1-6}$-alkyl or $C_{3-8}$-cycloalkyl, $R^3$ signifies $C_{1-12}$-alkyl or $C_{3-8}$-cycloalkyl, n signifies zero or 1, Y signifies $C_{1-7}$-alkylene or $C_{2-7}$-alkenylene, and Z, when n is zero, signifies $C_{3-8}$-cycloalkyl, a group —CH($C_6H_5$)O$R^4$, a group —CO$R^5$ or a group —CH$_2$N$^+$(CH$_3$)$_3$Hal$^-$, or Z, when n is 1, signifies amino % a group —O—CO$R^6$, a group —O$R^7$ or a group —S$R^8$, or Z, regardless of whether n is zero or 1, signifies alternatively aryl, heteroaryl, a group —COO$R^5$ or a group —CH(CH$_3$)O$R^4$, $R^4$ signifies hydrogen or acetyl, $R^5$ signifies hydrogen or $C_{1-6}$-alkyl, $R^6$ signifies $C_{1-6}$-alkyl, aryl or heteroaryl, $R^7$ signifies hydrogen, $C_{1-6}$-alkyl or acetyl, $R^8$ signifies $C_{1-6}$-alkyl, and Hal$^-$ signifies a halogen ion.

In the above definition of the astaxanthin derivatives of the formula I any alkyl or alkenyl group containing three or more carbon atoms can be straight chain or branched. This also applies to the $C_{1-7}$-alkylene or $C_{2-7}$-alkenylene (divalent) group signified by Y; thus the alkylene group can be for example methylene or di-, tri-, tetra-, penta-, hexa- or heptamethylene, or, respectively, ethylidene, propylidene (ethylmethylene), 1- or 2-methyl substituted ethylene and further mono- or multi-branched alkylene groups containing altogether up to seven carbon atoms. In addition for the straight chain or branched $C_{2-7}$-alkenylene group, this is understood to encompass alkenylene groups with one or (from $C_4$) more double bonds; examples of such alkenylene groups are those of the formulae —CH=CH—, —CH=CH—CH$_2$—, —CH=CH—(CH$_2$)$_3$— and —(CH=CH)$_2$—.

Any aryl group (a significance of Z or of $R^6$ in the group —O—CO$R^6$ signified by Z when n is 1) can be unsubstituted phenyl, naphthyl or a further multiring aromatic hydrocarbon group, or such a group featuring one or more substituents, particularly those substituents selected from $C_{1-4}$-alkyl, $C_{1-4}$-alkoxy, halogen and benzyloxy. Halogen indicates fluorine, chlorine, bromine or iodide. Examples of substituted phenyl groups are p-tolyl, 3-methoxyphenyl, 4-methoxyphenyl, 2,5-dimethoxyphenyl, 3,4-dimethoxyphenyl and 4-benzyloxyphenyl.

The expression "heteroaryl", also a significance of Z or of $R^6$ in the group —O—CO$R^6$, means a heterocyclic group of aromatic character featuring as ring member(s) one or more heteroatoms selected from oxygen, sulphur and nitrogen. Examples of such heteroaryl groups are 2- or 3-furyl, 2- or 3-thienyl and 4-pyridyl. As in the case of the aryl groups, the heteroaryl groups can be unsubstituted or substituted by one or more substituents as indicated hereinabove for the substituted aryl groups.

As regards the expression "residue of a protein-forming amino acid" (the significance of $R^1$ when not signifying hydrogen), this means that the pertinent group (a) in which $R^1$ has this significance is derived from any amino acid $H_2N$—CH($R^1$)—COOH, $R^1$ signifying the variable part of the amino acid molecule. Many examples of amino acids are given in, amongst other literature references, Organische Chemie, "Von den Grundlagen zur Forschung", Vol. 1, Ed. Salle+Sauerländer, pages 302-304 (Frankfurt 1988), the contents of which are appropriately incorporated herein. Where the amino acid is the simplest member glycine, the group (a) signifies —NH—CH$_2$—COO$R^2$, $R^1$ being hydrogen (and $R^2$ being any $C_{1-6}$-alkyl or $C_{3-8}$-cycloalkyl group). In the case of phenylalanine and methionine, the group (a) and $R^1$ signify —NH—CH($C_6H_5$)—COO$R^2$ and phenyl ($C_6H_5$), and —NH—CH(CH$_2$CH$_2$SCH$_3$)—COO$R^2$ and 2-methylthioethyl (CH$_2$CH$_2$SCH$_3$), respectively. Other examples of the group (a) and the "residue of the protein-forming amino acid" (significance of $R^1$) will not require specific elucidation.

Finally the halogen ion Hal$^-$ can be a fluoride, chloride, bromide or iodide ion, preferably a chloride ion, Cl$^-$ The astaxanthin derivatives of formula I can be in any possible isomeric form or in the form of mixtures of isomers, e.g. racemate mixtures.

Examples of specific astaxanthin derivatives of the formula I (with the appropriate significance of R), and thus according to the present invention, are:

astaxanthin-diethyldicarbonate (R is ethoxy),
astaxanthin-diethyldioxalate (R is ethoxycarbonyl),
astaxanthin-di(N-acetylglycinate) (R is acetylaminomethyl),
astaxanthin-dimaleinate (R is —CH=CH—COOH),
astaxanthin-disuccinate (R is —CH$_2$—CH$_2$—COOH),
astaxanthin-dimethyldisuccinate (R is —CH$_2$—CH$_2$—COOCH$_3$),
astaxanthin-diethyldisuccinate (R is —CH$_2$—CH$_2$—COOC$_2$H$_5$),
astaxanthin-diethyldiglycinedicarbamate (R is —NH—CH$_2$—COOC$_2$H$_5$),
astaxanthin-dinicotinate (R is 3-pyridyl),
astaxanthin-dimethioninedicarbamate (R is —NHCH(CH$_2$CH$_2$SCH$_3$)COOC$_2$H$_5$),
astaxanthin-diacetyldiglycolate (R is acetyloxymethyl),
astaxanthin-diphenylalaninedicarbamate (R is —NHCH(CH$_2$C$_6$H$_5$)COOC$_2$H$_5$),
astaxanthin-diethyldifumarate (R is —CH=CH—COOC$_2$H$_5$),
astaxanthin-di(2-furoate) (R is 2-furyl),
astaxanthin-dimethyldimalonate (R is —CH$_2$—COOCH$_3$),
astaxanthin-di(3-methylthiopropionate) (R is 3-methylthioethyl),
astaxanthin-dimethoxyacetate (R is methoxymethyl),
astaxanthin-di-[(2-thienyl)acetate] [R is (2-thienyl)methyl],
astaxanthin-dilactate (R is 1-hydroxyethyl),
astaxanthin-di(acetylmandelate) (R is α-acetyloxybenzyl) and
astaxanthin dibetainate [R is —CH$_2$N$^+$(CH$_3$)$_3$Cl$^-$].

Each of the above-named astaxanthin derivatives is preferably in the (all-E)-3,3'-rac isomeric form.

The six astaxanthin derivatives astaxanthin-diethyldicarbonate, -dimethyldisuccinate, -diethyldisuccinate, -dinicotinate, -dimethoxyacetate and -di-[(2-thienyl)acetate] are especially preferred ones in view of their stability and pigmentation properties.

The astaxanthin derivatives of the present invention can be manufactured in principle according to synthetic methods known per se for esterifications or amidations, according to the nature of the group R, whereby astaxanthin is reacted with the pertinent acid RCOOH as such or as its acid chloride RCOCl or acid anhydride (RCO)$_2$O or, in the cases where R signifies a group (a), with the appropriate N-carbonyl-amino acid ester of the formula OCNCH($R^1$)COO$R^2$.

These processes for producing the astaxanthin derivatives of the formula I represent a further aspect of the present invention.

In the case of esterification with an acid chloride or acid anhydride, the reaction is generally conducted in an inert solvent and in the presence of an organic base. As the solvent (which may instead act as a dispersion medium in the case of suspension rather than dissolution) there is conveniently used a lower halogenated hydrocarbon, e.g. methylene chloride or chloroform; a lower aliphatic or cyclic ether, e.g. diethyl ether, or tetrahydrofuran or dioxan, respectively; an aromatic hydrocarbon, e.g. toluene; or a lower aliphatic ketone, e.g. acetone. The base is suitably a lower trialkylamine, e.g. triethylamine; pyridine; or a di(lower alkyl) aminopyridine, e.g. dimethylaminopyridine. The molar ratio of astaxanthin:acid chloride or acid anhydride: base is conveniently in the range of 1:2-6:2-10. Moreover, the esterification is generally conducted in the temperature range of about −10° C. to about +100° C., preferably of about 25° C. to about 60° C., and most preferably of about 25° C. to about 40° C. Under such conditions the esterification is generally complete within about 1 to 24 hours, usually within about 2 to 6 hours, from the start of the reaction. It has been found to be advantageous to effect the esterification under an inert atmosphere, preferably using nitrogen or argon as the inert gas. Furthermore, where the (generally preferred) base triethylamine is employed, it has been found to be advantageous in the case of particularly slow reactions to augment said base with up to about 20% of its molar amount of 4-dimethylaminopyridine.

Where the acid itself is used to esterify the astaxanthin, the conditions are generally similar to those employed for esterifications with an acid chloride or anhydride in respect of the solvent/dispersion medium and reaction temperatures. However, in the present case a dehydrating agent is generally employed instead of a base. A particularly suitable dehydrating agent is dicyclohexylcarbodiimide. The molar ratio of astaxanthin:carboxylic acid: dehydrating agent is conveniently in the range of 1:2-6:2-7. Esterifications using the appropriate carboxylic acid are generally complete within a few minutes up to about 18 hours.

Finally, the production of the astaxanthin derivatives of formula I wherein R signifies a group (a), using the aforementioned N-carbonyl-amino acid ester as the one starting material, can likewise be effected using the kinds of solvents/dispersion media given above for the other two cases, and the reaction temperatures are also generally similar, viz. in the range generally from about −10° C. to about +120° C., preferably from about 25° C. to about 60° C., and most preferably from about 25° C. to about 40° C. In the present case, however, there may be used as an alternative to the kind of base used for the esterification with an acid chloride or anhydride a Lewis acid, e.g. boron trifluoride etherate or a tin or zinc salt, such as the respective chloride. The molar ratio of astaxanthin:N-carbonyl-amino acid ester is conveniently 1:2-4, preferably 1:2.2-2.4. In the case of using a base, particularly triethylamine or 4-dimethylaminopyridine, the amount of such basic catalyst relative to the amount of astaxanthin starting material, expressed in equivalents (based on 1 equivalent of astaxanthin) is generally in the range of about 0.5 to about 10.0 (triethylamine) or of about 0.1 to about 10.0 (4-dimethylaminopyridine). Where a Lewis acid, particularly zinc dichloride, is used instead of a basic catalyst, the amount of said Lewis acid relative to the amount of astaxanthin (1 equivalent) is generally in the range of about 0.05 to about 0.5, preferably in the range of about 0.1 to about 0.2 equivalents. Under such conditions the reaction in this case is generally complete after a much longer period, usually up to 72 hours. However, using zinc dichloride as the Lewis acid, for example, the reaction is generally complete in as short a period as from about 1 to about 3 hours.

In all these cases the product, i.e. the astaxanthin derivative of formula I, can be isolated and purified by methods known per se, e.g. by adding a solvent such as methanol to induce the separation of the crude product from the mixture after reaction, and crystallization of the collected crude product.

The pertinent acids RCOOH, acid chlorides RCOCl, acid anhydrides $(RCO)_2O$ and N-carbonyl-amino acid esters of the formula $OCNCH(R^1)COOR^2$ used as starting materials in the above-described processes for producing the astaxanthin derivatives of the formula I are either known compounds, or can be readily produced by processes analogous to the processes for producing the related known starting materials.

As indicated above, the astaxanthin derivatives of the present invention are useful as pigments in aquaculture, especially for the feed of aquatic animals, and accordingly are useful as the or a pigmenting agent in such feed.

Aquatic animals within the meaning of the present invention are fish, particularly marine, freshwater, anadromous or catadromous finfish, and crustacea species. Preferred fish for which the aforementioned feed for aquatic animals is very applicable are red sea bream, yellowtail, trout, salmon, tilapia, catfish and goldfish, Atlantic and Pacific salmon and trout being especially preferred. Preferred crustaceans are prawns, shrimps and crayfish.

For the realisation of their use as pigmenting agents for the feed of aquatic animals the astaxanthin derivatives may be incorporated in the feed by methods known per se in the art of feed formulation and processing, in principle by admixture with at least some of the components of the final feed at an appropriate stage of its manufacture. The astaxanthin esters are normally incorporated as a formulation, particularly a water-dispersible formulation. Such a formulation can be produced in principle by first dissolving the astaxanthin derivative in a plant or vegetable oil or fat, e.g. corn oil, or in an organic solvent, e.g. an alcohol, an aliphatic ether, a halogenated aliphatic hydrocarbon such as methylene chloride, or an aliphatic ester, or in a mixture of both a plant or vegetable oil or fat and an organic solvent. The dissolution can be effected in a broad temperature range, e.g. in the range from room temperature to about 150° C. In the case of using methylene chloride as the organic solvent for the dissolution, this can be effected at room temperature or at temperatures up to about 30° C., or at higher temperatures on application of elevated pressure. The use of relatively low temperatures when using methylene chloride or an alternative solvent is particularly advantageous for preventing the astaxanthin derivative from being subjected to unnecessarily high dissolution temperatures, and so represents an economical and mild processing. Moreover, methylene chloride in particular dissolves the astaxanthin derivatives so readily that further economic savings are gained through the use of relatively low volumes of this solvent; as one result thereof, less of the solvent needs to be removed by evaporation and then disposed of or recycled, and as another, the processing of the lower solution volume can be effected more rapidly. After completion of the dissolution the solution is normally emulsified with an aqueous solution of a protective colloid, e.g. a plant or animal protein such as a gelatin, particularly fish gelatin; a carbohydrate; polysaccharide; or a ligninsulphonate. The solvent and water are then at least partially removed, thus affording the formulation as a concentrated emulsion. Before the actual incorporation in the feed the concentrated emulsion can either be directly spray-dried by conventional spray-drying techniques or spray-dried into fluidized starch or an alternative carrier, e.g. calcium silicate, again by conventional techniques. The product of such spray-drying consists of beadlets, which, apart from the astaxanthin derivative itself contain components from the previous processing, e.g. oil, protective colloid, starch etc., and which may contain up to about 25% by weight of said derivative; the content of any oil present is generally in the range from about 0.5% to about 50% by weight, the content of matrix material (principally protective colloid) generally in the range from about 50% to about 80% by weight, and the content of any carrier material from the spray-drying (starch, calcium silicate etc.) generally from about 10% to about 25% by weight. Apart from the aforementioned materials, the beadlets may contain relatively minor amounts of stabilizers, emulsifying agents and other conventional formulation aids. The preparation is conventionally then mixed with other components of the feed, such as fish oil and fish meal, and the mixture is subjected to a hydrothermal process, e.g. pelleting or extrusion, with application of high shear, to produce the feed for aquatic animals, supplemented with the astaxanthin derivative, in pelleted form. During such processing (pelleting, extrusion) temperatures in the range of about 70 to about 150° C., especially about 90 to about 130° C., and pressures in the range of about 10 to about 100 bar, especially about 20 to about 40 bar, may be reached. Accordingly, it is important that the incorporated pigment, in this case the astaxanthin derivative of the formula I, is able to sustain such high temperatures and pressures without excessive degradation. The content of this pigmenting agent in a so-manufactured fish feed is generally in the range of about 30 to about 100 ppm.

Further information on fish feed formulation and processing is available in for example American Feed Industry Ass., Feed Manufacturing Technology IV, 1994, pp. 509-515.

As an alternative to forceably subjecting the incorporated astaxanthin derivative to the harsh temperature and pressure conditions involved in such an above-described hydrothermal process, the formulation for incorporation may be diluted in water and then added to and admixed with the feed for aquatic animals after said feed has been subjected to the hydrothermal process.

Further aspects of the present invention are formulations containing astaxanthin derivatives of the present invention for incorporation into feed for aquatic animals, and such feed containing an effective amount of the astaxanthin derivative as a pigmenting agent, particularly a feed for aquatic animals containing from about 30 to about 100 ppm of such an astaxanthin derivative.

The invention is illustrated by the following Examples of the preparation of the astaxanthin derivatives of the formula I.

EXAMPLE 1

(all-E)-3,3'-rac-Astaxanthin-di(L-lactate)

212 g of lactic acid and 0.84 g of p-toluenesulphonic acid were diluted in 2.3 kg of methylene chloride at 4° C. 260.3 g of dihydropyrane are then added within 38 minutes. After stirring the mixture for a further 10 minutes the temperature was increased to 20° C. and the stirring was continued for a further 1.5 hours. The solution was thereafter washed with three 900 ml portions of 0.2 M aqueous potassium hydroxide solution. The basic water phase was removed and the organic phase was washed with two 350 ml portions of water. The water phase was washed with methylene chloride. The organic phases were then combined and dried with anhydrous sodium sulphate. The solvent was evaporated until an oily phase, consisting of tetrahydropyranyl-lactic acid, remained.

73.26 g of tetrahydropyranyl-lactic acid, 47.22 g of dicyclohexylcarbodiimide and 0.84 g of 4-dimethylaminopyridine were added to a stirred solution of 9.2 g of astaxanthin in 1782.4 g of tetrahydrofuran at 25° C. under inert and dry conditions. After stirring for about 16 hours, the precipitated dicyclohexylurea was removed by filtration. The solvent of the remaining solution was distilled off under reduced pressure. The residue was then dissolved in 615.8 g of methylene chloride, and the solution added to 750 ml of a 2 molar solution of sulphuric acid already warmed to 27° C. After being stirred for 1.5 hours, the organic phase of the two-phase mixture was separated. The aqueous phase was extracted with two 75 ml portions of methylene chloride, and the combined organic phases were dried with 95.83 g of anhydrous sodium sulphate, filtered and evaporated to dryness.

The residue was diluted with 385.9 g of pyridine at 22° C. and 210 g of water were added within 7 minutes The temperature rose to 32° C. After adding a further 298.9 g of water, violet crystals precipitated. After being stirred for 2 hours, the crystals were filtered off and dried under reduced pressure for about 16 hours.

The crystals were diluted with 291 g of methylene chloride, and the solution was added to a 7.9 molar aqueous solution of sulphuric acid already warmed to 27° C. After stirring for 1.5 hours 350 ml of water were added, and the organic phase was separated. The organic phase was washed with two 200 ml portions water. The aqueous phases were washed with 200 ml of methylene chloride, and the organic phases were combined. The combined organic phase was then dried with 104.8 g of anhydrous sodium sulphate, filtered and evaporated to dryness.

The resulting crystals were diluted in 228 g of toluene at room temperature. After addition of 35.2 g of hexane and 10 minutes stirring red crystals precipitated. A second portion of 14 g of hexane was then added, and the suspension stirred, filtered, washed with 22 g of hexane and dried under high reduced pressure for about 16 hours.

The crystals were diluted with 246 g of methylene chloride. 276 g of hexane were added in six portions until red crystals precipitated. After filtration and drying 6 g of (all-E)-3,3'-rac-astaxanthin-di(L-lactate) (HPLC area %: 95%) were obtained.

EXAMPLE 2

(all-E)-3,3'-rac-Astaxanthin-diethyldioxalate 56 ml of triethylamine and 4.99 g of 4-dimethylaminopyridine were added to a stirred slurry of 47.75 g of astaxanthin in 1.6 l of methylene chloride at 25° C. under inert and dry conditions. 30 minutes after the dropwise addition of 45.9 ml of oxalic acid ethyl ester chloride at 25° C. the reaction was complete. The excess acid chloride was then destroyed by adding methanol. After neutralization with 12 ml of acetic acid the reaction mixture was evaporated to dryness. The residue was dissolved in 1 l of methylene chloride, extracted with three 500 ml portions of water and the organic phase dried over anhydrous sodium sulphate. The product was precipitated from the dried solution by the addition of 1 l of methanol. After filtration, washing with methanol and drying 53.2 g (83.4% yield) of (all-E)-3,3'-rac-astaxanthin-diethyldioxalate were obtained as dark red crystals (HPLC area %: 98.1%).

EXAMPLE 3

(all-E)-3,3'-rac-Astaxanthin-diethyldicarbonate 105 ml of triethylamine and 9.35 g of 4-dimethylaminopyridine were added at reflux temperature to a stirred solution of 29.84 g of astaxanthin in 1 l of methylene chloride under dry and inert conditions. In intervals of 15 minutes 24.31 ml of ethyl chloroformate were introduced in six equal portions. After a total of 2.5 hours, the reaction mixture was cooled to 25° C., and the excess acid chloride was destroyed by the addition of methanol. After evaporation to dryness, the residue was dissolved in 500 ml of methylene chloride and extracted three times with water, and the organic phase was dried over anhydrous sodium sulphate. The product was precipitated from a reduced volume of 250 ml by the addition of 100 ml of methanol. After filtration, washing with methanol and drying 33.69 g (90.9% yield) of (all-E)-3,3'-rac-astaxanthin-diethyldicarbonate were obtained as dark red crystals (HPLC area %: 89.8%).

EXAMPLE 4

(all-E)-3,3'-rac-Astaxanthin-di(N-acetylglycinate)

4.73 g of N-acetylglycine, 5.97 g of astaxanthin, 249 mg of 4-dimethylaminopyridine and 40 ml of methylene chloride were mixed under dry and inert conditions. At 25° C. a solution of N,N-dicyclohexylcarbodiimide in 40 ml of methylene chloride was then added with stirring. After 17 hours the methylene chloride was replaced by chloroform (105 ml of solvent mixture was distilled off). The resulting hot suspension of crystals (internal temperature 60° C.) was then filtered and the crystals (dicyclohexylurea) washed with a total amount of 100 ml of chloroform. The filtrate was concentrated to a volume of 75 g, and the product crystallized by the addition of 150 ml of methanol. After washing and drying 6.34 g (79.7% yield) of (all-E)-3,3'-rac-astaxanthin-di(N-acetylglycinate) were obtained (HPLC area %: 95.5%).

EXAMPLE 5

(all-E)-3,3'-rac-Astaxanthin-dimethyldisuccinate 17.5 ml of triethylamine and 1.56 g of 4-dimethylaminopyridine were added at reflux temperature to a stirred solution of 14.92 g of astaxanthin in 500 ml of tetrahydrofuran under inert and dry conditions. Over a period of 70 minutes 11.0 ml of methyl succinoyl chloride were continuously introduced. After a further hour, the reaction mixture was cooled to 25° C., and 125 ml of methanol were added to destroy the excess acid chloride. After extraction with methylene chloride/water (1:1) and chromatography on silica gel with the eluent toluene/n-hexane/ethyl acetate in the ratio 2:2:1 the product was isolated by crystallization from methanol. After drying 10.29 g (49.9% yield) of (all-E)-3,3'-rac-astaxanthin dimethyldisuccinate were obtained as dark red crystals (HPLC area %: 79.3%). After recrystallization from methylene chloride/methanol a product of 98% purity by HPLC was obtained.

EXAMPLE 6

(all-E)-3,3-rac-Astaxanthin-diethylglycincarbamate 1.19 g of astaxanthin, 0.55 ml of ethylisocyanoacetate and 56 mg of zinc dichloride in 10 ml of methylene chloride were mixed with stirring at 25° C. to a slurry under inert and dry conditions. After one hour the reaction was complete. The product was crystallized by the addition of 25 ml of acetone. The resulting violet crystals were isolated by filtration. After washing with acetone/methylene chloride in the ratio 5:2 and drying, 1.59 g (91.8% yield) of (all-E)-3,3'-rac-astaxanthin-diethylglycincarbamate were obtained (HPLC area %: 98.4%).

EXAMPLE 7

((all-E))-3,3'-rac-Astaxanthin-diacetyldiglycolate 30.44 g of astaxanthin, 24.33 g of acetylglycolic acid and 1.27 g of 4-dimethylaminopyridine in 200 ml of methylene chloride were mixed at 25° C. with stirring to a slurry. under dry and inert conditions. Within 10 minutes a solution of 46.77 g of N,N-dicyclohexylcarbodiimide in 200 ml of methylene chloride was added, causing an exothermic reaction. After one hour the reaction was complete. The dicyclohexylurea was filtered off, the filtrate concentrated and the product crystallized by the addition of methanol. After filtration and drying, 38.96 g (95.8% yield) of (all-E)-3,3'-rac-astaxanthin-diacetylglycolate were isolated as dark red crystals (HPLC area %: 95.8%).

EXAMPLE 8

Astaxanthin-diethyldisuccinate

Under dry and inert conditions 2.98 g of astaxanthin and 1.0 ml of pyridine were added to 25 ml of methylene chloride at 25° C. with stirring. 1.8 ml of ethyl succinoyl chloride were then added within 15 minutes to the stirred suspension at 25° C. After 3 hours the esterification was complete and the methylene chloride solvent was replaced with methanol by azeotropic distillation. 5 ml of water were added to the remaining crystalline suspension in about 50 ml of methanol. The suspension was boiled for 1 hour at reflux temperature (promoting Z,E-isomerization). After cooling to 25° C., the crystals were filtered off, washed with 20 ml of methanol and dried. 3.66 g (85.9% yield) of crude astaxanthin-diethyldisuccinate were obtained as dark violet crystals (HPLC area %: 91.8% all-E, 5.0% Z-isomers).

EXAMPLE 9

Astaxanthin-dimaleinate

Under dry and inert conditions a solution of 17 g of triethylamine in 20 ml of methylene chloride was added to a stirred suspension of 10 g maleic anhydride and 20 g astaxanthin in 300 ml of methylene chloride at 25° C. After 90 minutes the reaction was complete and the resulting solution was extracted successively with 250 ml of 3N hydrochloric acid and brine. The final product was precipitated by the addition of sufficient n-hexane. After filtration, washing with n-hexane and drying, 27 g (almost 100% yield) of pure astaxanthin-dimaleinate were obtained as dark red crystals (HPLC area %: approx. 97.7% all-E).

EXAMPLE 10

Astaxanthin-disuccinate

Under dry and inert conditions 59.69 g of astaxanthin, 25.27 g of succinic anhydride, 70.04 ml of triethylamine and 3.12 g of 4-dimethylaminopyridine (DMAP) were suspended in 500 ml of methylene chloride at 25° C. After stirring for about 16 hours the conversion of astaxanthin to its diester was complete. The resulting solution was acidified with 500 ml of 1N hydrochloric acid and extracted with 420 ml of methylene chloride. The organic layer was neutralized by washing with 750 ml of water, dried over anhydrous sodium sulphate and then concentrated by evaporation. The product was crystallized by the addition of sufficient n-hexane to the viscous residue. After filtration, washing with n-hexane and drying, 79.06 g (99.2% yield) of pure astaxanthin-disuccinate were obtained as dark red crystals (HPLC area %: 97.4% all-E).

EXAMPLE 11

Astaxanthin-dinicotinate

Under dry and inert conditions 28.05 g of nicotinoyl chloride hydrochloride were added portionwise to a slurry of 35.81 g of astaxanthin, 65.9 ml of triethylamine and 5.83 g of 4-dimethylaminopyridine in 300 ml of methylene chloride at a temperature in slight excess of 25° C. After a total of 5 hours stirring at 25-30° C., the triethylamine was neutralized by the addition of 26.8 ml of acetic acid. The reaction mixture was then extracted with three 400 ml portions of water, and the organic layer was backwashed with two 200 ml portions of methylene chloride. After concentration of the collected organic layer to a weight of 240 g, the crystallization of the product was promoted by the addition of 480 ml of methanol. The suspension was stirred for about 16 hours at 25° C. to complete the precipitation of the crystals. After filtration, washing with two 30 ml portions of methanol and drying, 53.02 g of crude, dark grey crystals were obtained. The crude crystals were purified by recrystallization from methylene chloride/methanol to afford 48.83 g (approx. 100% yield) of pure astaxanthin-dinicotinate (HPLC area %: 98.9% all-E; 9% methylene chloride).

EXAMPLE 12

Astaxanthin-di[(R)—O-acetylmandelate]

Under dry and inert conditions a solution of 24.8 g of N,N-dicyclohexylcarbodiimide in 120 ml of methylene chloride was added over a period of 30 minutes to a stirred slurry of 25.36 g of astaxanthin, 20 g of (R)—O-acetylmandelic acid and 1.5 g of 4-dimethylaminopyridine in 250 ml of methylene chloride at 25° C. After a further 30 minutes of stirring at 25° C. the reaction was complete and the resulting crystalline slurry was filtered (after drying: 23.31 g of N,N-dicyclohexylurea). The filtrate was concentrated to a weight of 250 g and the crude product was crystallized by the addition of 750 ml of methanol at 0° C. After further stirring at 0° C. for 30 minutes, the suspension was filtered and the crystals were washed with two 70 ml portions of methanol/methylene chloride (8:2) at 0° C. The dried crude crystals (37.87 g) were purified by recrystallization from methylene chloride/methanol. 32.09 g (79.6% yield) of pure astaxanthin-di[(R)—O-acetylmandelate] were obtained as red crystals (HPLC area %: 99.6% all-E).

EXAMPLE 13

Astaxanthin-di-[(2-thienyl)acetate]

Under dry and inert conditions a solution of 42.52 g of N,N-dicyclohexylcarbodiimide in 240 ml of methylene chloride was added over a period of 30 minutes to a stirred slurry of 35.81 g of astaxanthin, 26.1 g of (2-thienyl)acetic acid and 1.5 g of 4-dimethylaminopyridine in 360 ml of methylene chloride at 25° C. After stirring for 3 hours at 25° C. the reaction was complete and N,N-dicyclohexylurea could be separated by filtration. After solvent exchange from methylene chloride to methanol, filtration of the resulting suspension, washing of the crystals with methanol and drying, 50.73 g of crude crystalline product were isolated. The crystals were purified by dissolving them in 200 ml of methylene chloride followed by a solvent exchange to methanol. 46.94 g (92.6% yield) of pure astaxanthin-di[(2-thienyl)acetate] were isolated after filtration, washing with methanol and drying (HPLC area %: 99.5% all-E).

EXAMPLE 14

Astaxanthin-di(3-methylthiopropionate)

Under dry and inert conditions a solution of 42.52 g of N,N-dicyclohexylcarbodiimide in 240 ml of methylene chloride was added over a period of 75 minutes to a stirred slurry of 35.81 g of astaxanthin, 21.8 g of 3-methylthiopropionic acid and 1.5 g of 4-dimethylaminopyridine in 360 ml of methylene chloride at 25° C. After stirring for 1 hour at 25° C. the reaction was complete and N,N-dicyclohexylurea could be separated by filtration. After solvent exchange from methylene chloride to methanol, filtration of the resulting suspension, washing of the crystals with methanol and drying, 47.75 g of crude product were isolated. After purification from methylene chloride/methanol, 44.98 g (93.6% yield) of pure astaxanthin-di(3-methylthiopropionate) were obtained as dark red crystals (HPLC area %: about 100% all-E).

EXAMPLE 15

Astaxanthin-di(2-furoate)

Under dry and inert conditions 21.09 ml of 2-furoyl chloride were added over a period of 30 minutes to a stirred suspension of 41.78 g of astaxanthin, 29.42 ml of triethylamine and 2.62 g of 4-dimethylaminopyridine in 1.4 l of methylene chloride at 25° C. After 2 hours stirring at 25° C. the reaction was complete. 500 ml of methanol were then added cautiously and the methylene chloride was distilled off and replaced by methanol. The resulting crystalline suspension was stirred at 25° C. for about 16 hours and then filtered. After washing with 100 ml of methanol and drying, 52.76 g (96.0% yield) of pure astaxanthin-di(2-furoate) were obtained (HPLC area %: about 100%).

The invention claimed is:

1. A process for producing a formulation comprising an astaxanthin derivative of the general formula I

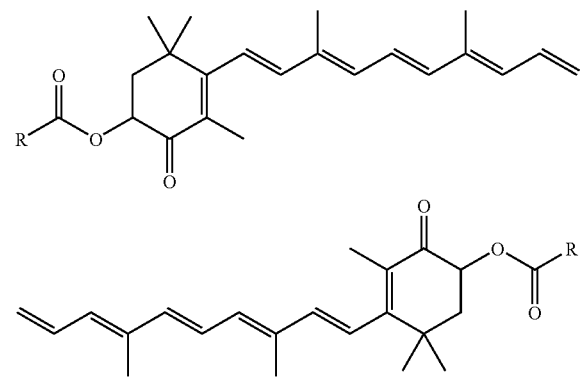

wherein
R is in each case a group (a), (b) or (c)
—NH—CH($R^1$)—COO$R^2$ (a)
—O$R^3$ (b)
—(Y)$_n$—Z (c)
$R^1$ signifies hydrogen or the residue of a protein-forming amino acid,
$R^2$ signifies $C_{1-6}$-alkyl or $C_{3-8}$-cycloalkyl,
$R^3$ signifies $C_{1-12}$-alkyl or $C_{3-8}$-cycloalkyl,
n signifies zero or 1,
Y signifies $C_{1-7}$-alkylene or $C_{2-7}$-alkenylene,
and Z when n is zero, signifies $C_{3-8}$-cycloalkyl, a group —CH($C_6H_5$)O$R^4$, a group —CO$R^5$ a group —$CH_2N^+(CH_3)_3$Hal$^-$,
or Z when n is 1, signifies amino, a group —O—CO$R^6$, a group —O$R^7$ or a group —S$R^8$,
or Z regardless of whether n is zero or 1, signifies alternatively aryl, heteroaryl, a group —COO$R^5$ or a group —CH($CH_3$)O$R^4$,
$R^4$ signifies hydrogen or acetyl,
$R^5$ signifies hydrogen or $C_{1-6}$-alkyl,
$R^6$ signifies $C_{1-6}$-alkyl, aryl or heteroaryl,
$R^7$ signifies hydrogen, $C_{1-6}$-alkyl or acetyl,
$R^8$ signifies $C_{1-6}$-alkyl, and
Hal$^-$ signifies a halogen ion;
wherein the process comprises dissolving the astaxanthin derivative in a plant or vegetable oil or fat, or in an organic solvent, or in a mixture of both a plant or vegetable oil or fat and an organic solvent, emulsifying the solution with an aqueous solution of a protective colloid, at least partially removing the solvent and water to afford a concentrated emulsion, and spray-drying the concentrated emulsion to finally produce a formulation suitable for incorporation in a feed for aquatic animals.

2. A process according to claim 1, wherein the astaxanthin derivative is dissolved in methylene chloride as the solvent.

3. An astaxanthin derivative of the general formula I

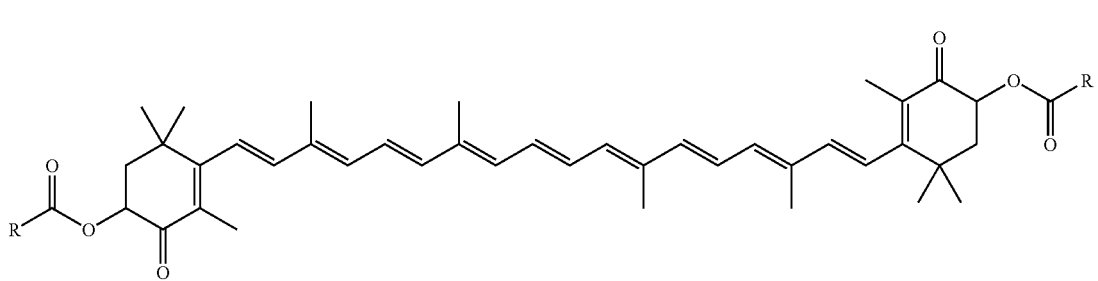

selected from the group consisting of astaxanthin-diethyldicarbonate, -dimethyldisuccinate, -diethyldisuccinate, -dinicotinate, -dimethoxyacetate and di-[(2-thienyl)acetate] in the (all-E)-3,3'-rac isomeric form.

4. A process for producing an aquatic animal feed supplement comprising an astaxanthin derivative of the general formula I

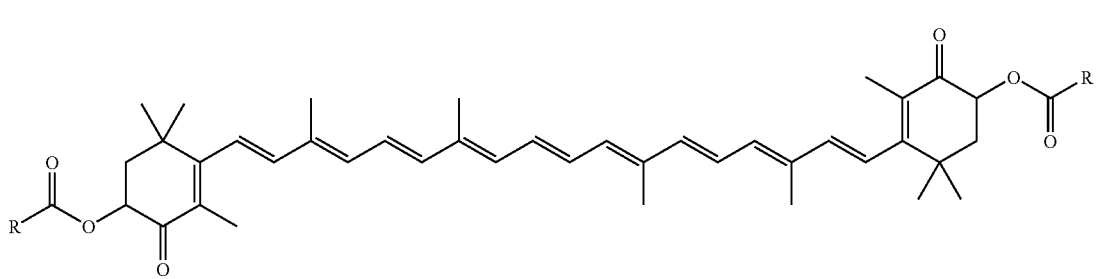

selected from the group consisting of:
astaxanthin-diethyldicarbonate (R is ethoxy),
astaxanthin-diethyldioxalate (R is ethoxycarbonyl),
astaxanthin-di(N-acetylglycinate) (R is acetylaminomethyl),
astaxanthin-dimaleinate (R is —CH=CH—COOH),
astaxanthin-disuccinate (R is —CH$_2$—CH$_2$—COOH),
astaxanthin-dimethyldisuccinate (R is —CH$_2$—CH$_2$—COOCH$_3$),
astaxanthin-diethyldisuccinate (R is —CH$_2$—CH$_2$—COOC$_2$H$_5$),
astaxanthin-diethyldiglycinedicarbamate (R is —NH—CH$_2$—COOC$_2$H$_5$),
astaxanthin-dinicotinate (R is 3-pyridyl),
astaxanthin-dimethioninedicarbamate (R is —NHCH(CH$_2$CH$_2$SCH$_3$)COOC$_2$H$_5$),
astaxanthin-diacetyldiglycolate (R is acetyloxymethyl),
astaxanthin-diphenylalaninedicarbamate (R is —NHCH(CH$_2$C$_6$H$_5$)COOC$_2$H$_5$),
astaxanthin-diethyldifumarate (R is —CH=CH—COOC$_2$H$_5$),
astaxanthin-di(2-furoate) (R is 2-furyl),
astaxanthin-dimethyldimalonate (R is —CH$_2$—COOCH$_3$),
astaxanthin-di(3-methylthiopropionate) (R is 3-methylthioethyl),
astaxanthin-dimethoxyacetate (R is methoxymethyl),
astaxanthin-di-[(2-thienyl)acetate] (R is (2-thienyl)methyl),
astaxanthin-dilactate (R is 1-hydroxyethyl),
astaxanthin-di(acetylmandelate) (R is α-acetyloxybenzyl), and
astaxanthin dibetainate (R is —CH$_2$N$^+$(CH$_3$)$_3$ Cl$^-$);
wherein the process comprises dissolving the astaxanthin derivative in a plant or vegetable oil or fat, or in an organic solvent, or in a mixture of both a plant or vegetable oil or fat and an organic solvent, emulsifying the solution with an aqueous solution of a protective colloid, at least partially removing the solvent and water to afford a concentrated emulsion, and spray-drying the concentrated emulsion to finally produce a formulation suitable for incorporation in a feed for aquatic animals.

5. A process according to claim 4, wherein the astaxanthin derivative is in the (all-E)-3,3'-rac isomeric form.

6. A process according to claim 4, wherein the astaxanthin derivative is dissolved in methylene chloride as the solvent.

7. A process according to claim 5, wherein the astaxanthin derivative is dissolved in methylene chloride as the solvent.

8. A supplemented feed for aquatic animals comprising "an aquatic animal feed supplement comprising an astaxanthin derivative of the general formula I wherein
R is in each case a group (a), (b) or (C)
—NH—CH(R$^1$)—COOR$^2$ (a)
—OR$^3$ (b)
—(Y)$_n$—Z (c)
R$^1$ signifies hydrogen or the residue of a protein-forming amino acid,
R$^2$ signifies C$_{1-6}$-alkyl or C$_{3-8}$-cycloalkyl,
R$^3$ signifies C$_{1-12}$-alkyl or C$_{3-6}$-cycloalkyl,
n signifies zero or 1,
Y signifies C$_{1-7}$-alkylene or C$_{2-7}$-alkenylene,
and Z when n is zero, signifies C$_{3-8}$-cycloalkyl, a group —CH(C$_6$H$_5$)OR$^4$, a group —COR$^5$ or a group —CH$_2$N$^-$(CH$_3$)$_3$Hal$^-$,
or Z when n is 1, signifies amino, a group —O—COR$_6$, a group —OR$^7$ or a group —SR$^8$,
or Z regardless of whether n is zero or 1, signifies alternatively aryl, heteroaryl, a group —COOR$^5$ or a group —CH(CH$_3$)OR$^4$,
R$^4$ signifies hydrogen or acetyl,
R$^5$ signifies hydrogen or C$_{1-6}$-alkyl,
R$^6$ signifies C$_{1-6}$-alkyl, aryl or heteroaryl,
R$^7$ signifies hydrogen, C$_{1-8}$-alkyl or acetyl,
R$^8$ signifies C$_{1-6}$-alkyl, and
Hal$^-$ signifies a halogen ion,
and a plant or vegetable oil or fat, an organic solvent, or a mixture of both a plant or vegetable oil or fat and an organic solvent;" in admixture with a feed for aquatic animals, wherein the astaxanthin derivative is selected from the group consisting of:
astaxanthin-diethyldicarbonate (R is ethoxy),
astaxanthin-diethyldioxalate (R is ethoxycarbonyl),
astaxanthin-di(N-acetylglycinate) (R is acetylaminomethyl),
astaxanthin-dimaleinate (R is —CH=CH—COOH),
astaxanthin-disuccinate (R is —CH$_2$—CH$_2$—COOH),
astaxanthin-dimethyldisuccinate (R is —CH$_2$—CH$_2$—COOCH$_3$),
astaxanthin-diethyldisuccinate (R is —CH$_2$—CH$_2$—COOC$_2$H$_5$),
astaxanthin-diethyldiglycinedicarbamate (R is —NH—CH$_2$—COOC$_2$H$_5$),
astaxanthin-dinicotinate (R is 3-pyridyl),
astaxanthin-dimethioninedicarbamate (R is —NHCH(CH$_2$CH$_2$SCH$_3$)COOC$_2$H$_5$),
astaxanthin-diacetyldiglycolate (R is acetyloxymethyl), astaxanthin-diphenylalaninedicarbamate (R is —NHCH(CH$_2$C$_6$H$_5$)COOC$_2$H$_5$), astaxanthin-diethyldifumarate (R is —CH=CH—COOC$_2$H$_5$), astaxanthin-di(2-furoate) (R is 2-furyl), astaxanthin-dimethyldimalonate (R is —CH$_2$—COOCH$_3$), astaxanthin-di(3-methylthiopropionate) (R is 3-methyithioethyl), astaxanthin-dimethoxyacetate (R is methoxymethyl)

astaxanthin-di-[(2-thienyl)acetate] (R is (2-thienyl)methyl), astaxanthin-dilactate (R is 1-hydroxyethyl), astaxanthin-di(acetylmandelate) (R is α-acetyloxybenzyl), and astaxanthin dibetainate (R is —CH$_2$N$^+$(CH$_3$)$_3$ Cl$^-$).

9. A supplemented feed for aquatic animals according to claim 8, wherein the astaxanthin derivative is in the (alI-E)-3,3'-rac isomeric form.

10. A feed for aquatic animals according to claim 8, containing the astaxanthin derivative in an amount in the range of about 30 to about 100 ppm.

11. A feed for aquatic animals according to claim 9, containing the astaxanthin derivative in an amount in the range of about 30 to about 100 ppm.

12. A process for producing a feed for aquatic animals, which feed comprises an astaxanthin derivative of the general formula I astaxanthin-disuccinate (R is —CH$_2$—CH$_2$—COOH), astaxanthin-dimethyldisuccinate (R is —CH$_2$—CH$_2$—COOCH$_3$), astaxanthin-diethyldisuccinate (R is —CH$_2$—CH$_2$—COOC$_2$H$_5$), astaxanthin-diethyldiglycinedicarbamate (R is —NH—CH$_2$—COOC$_2$H$_5$), astaxanthin-dinicotinate (R is 3-pyridyl), astaxanthin-dimethioninedicarbamate (R is —NHCH(CH$_2$CH$_2$SCH$_3$)COOC$_2$H$_5$), astaxanthin-diacetyldiglycolate (R is acetyloxymethyl), astaxanthin-diphenylalaninedicarbamate (R is —NHCH(CH$_2$C$_6$H$_5$)COOC$_2$H$_5$), astaxanthin-diethyldifumarate (R is —CH=CH—COOC$_2$H$_5$), astaxanthin-di(2-furoate) (R is 2-furyl), astaxanthin-dimethyldimalonate (R is —CH$_2$—COOCH$_3$), astaxanthin-di(3-methylthiopropionate) (R is 3-methylthioethyl), astaxanthin-dimethoxyacetate (R is methoxymethyl), astaxanthin-di-[(2-thienyl)acetate] (R is (2-thienyl)methyl), astaxanthin-dilactate (R is 1-hydroxyethyl), astaxanthin-di(acetylmandelate) (R is α-acetyloxybenzyl), and astaxanthin dibetainate (R is —CH$_2$N$^+$(CH$_3$)$_3$ Cl$^-$);

wherein the process comprises incorporating the astaxanthin derivative as a formulation in the feed by admixture of said formulation with at least some of the components of the final feed at an appropriate stage of its manufacture and subjecting the mixture containing the astaxanthin derivative to a hydrothermal process, thus producing the feed supplemented with the astaxanthin derivative.

13. A process according to claim 12, wherein the astaxanthin derivative is in the (all-E)-3,3'-rac isomeric form.

14. A process according to claim 12, wherein the feed contains the astaxanthin derivative in an amount in the range of about 30 to about 100 ppm.

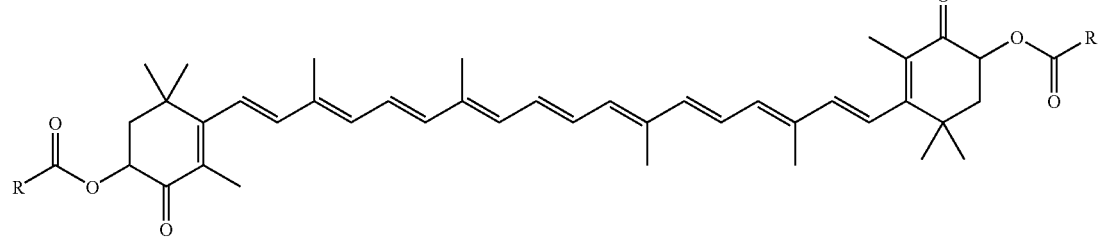

selected from the group consisting of:
astaxanthin-diethyldicarbonate (R is ethoxy),
astaxanthin-diethyldioxalate (R is ethoxycarbonyl),
astaxanthin-di(N-acetylglycinate) (R is acetylaminomethyl),
astaxanthin-dimaleinate (R is —CH=CH—COOH), 15. A process according to claim 13, wherein the feed contains the astaxanthin derivative in an amount in the range of about 30 to about 100 ppm.

16. A process according to claim 12, wherein the formulation is a water-dispersible formulation.

* * * * *